(12) United States Patent
Park et al.

(10) Patent No.: US 12,017,978 B2
(45) Date of Patent: Jun. 25, 2024

(54) METHOD FOR PREPARING ISOPROPYL ALCOHOL

(71) Applicant: LG CHEM, LTD., Seoul (KR)

(72) Inventors: Sa Eun Park, Daejeon (KR); Tae Woo Kim, Daejeon (KR); Sung Kyu Lee, Daejeon (KR)

(73) Assignee: LG Chem, Ltd., Seoul (KR)

( * ) Notice: Subject to any disclaimer, the term of this patent is extended or adjusted under 35 U.S.C. 154(b) by 426 days.

(21) Appl. No.: 17/432,022

(22) PCT Filed: Nov. 25, 2020

(86) PCT No.: PCT/KR2020/016764
§ 371 (c)(1),
(2) Date: Aug. 18, 2021

(87) PCT Pub. No.: WO2021/261682
PCT Pub. Date: Dec. 30, 2021

(65) Prior Publication Data
US 2022/0340510 A1    Oct. 27, 2022

(30) Foreign Application Priority Data

Jun. 23, 2020 (KR) .................. 10-2020-0076555

(51) Int. Cl.
*C07C 29/76* (2006.01)
*C07C 29/04* (2006.01)
*C07C 29/80* (2006.01)

(52) U.S. Cl.
CPC .............. *C07C 29/76* (2013.01); *C07C 29/04* (2013.01); *C07C 29/80* (2013.01)

(58) Field of Classification Search
CPC ..................... C07C 29/04; C07C 29/74–78
See application file for complete search history.

(56) References Cited

U.S. PATENT DOCUMENTS

| 4,469,903 A | 9/1984 | Schmidt |
| 2012/0016164 A1 | 1/2012 | Kohnz et al. |

FOREIGN PATENT DOCUMENTS

| CN | 1134410 A | 10/1996 |
| CN | 107501042 A | 12/2017 |
| CN | 109438179 A | 3/2019 |

(Continued)

*Primary Examiner* — Medhanit W Bahta
(74) *Attorney, Agent, or Firm* — Bryan Cave Leighton Paisner LLP

(57) ABSTRACT

A method for preparing isopropyl alcohol including: feeding a feed stream containing a propylene monomer and water to a reaction unit, where the propylene monomer and the water react to form a reaction product containing isopropyl alcohol, the propylene monomer, and the water; feeding each of a first discharge stream and a second discharge stream discharged from the reaction unit to a stripper, where the first discharge stream contains a vapor-phase reaction product, which is condensed through a first heat exchanger and fed to the stripper in a liquid-phase, and wherein the second discharge stream contains a liquid-phase reaction product; and separating a top discharge stream and a bottom discharge stream from the stripper, wherein the top discharge stream contains the propylene monomer and the bottom discharge stream contains the water and the isopropyl alcohol.

12 Claims, 2 Drawing Sheets

(56) References Cited

FOREIGN PATENT DOCUMENTS

| | | | |
|---|---|---|---|
| EP | 2939995 A1 * | 11/2015 | ............. C07C 29/04 |
| EP | 2939995 A1 | 11/2015 | |
| JP | 3693404 B2 | 9/2005 | |
| JP | 2016-515930 A | 6/2016 | |
| JP | 6681676 B2 | 4/2020 | |
| KR | 10-0219006 B1 | 9/1999 | |
| KR | 10-2019-0019060 A | 2/2019 | |
| KR | 10-2020-0027410 A | 3/2020 | |
| WO | 2017/217279 A1 | 12/2017 | |

* cited by examiner

METHOD FOR PREPARING ISOPROPYL ALCOHOL

CROSS-REFERENCE TO RELATED APPLICATIONS

This application is a U.S. national stage of international Application No. PCT/KR2020/016764 filed on Nov. 25, 2020, and claims benefit of priority to Korean Patent Application No. 10-2020-0076555 filed on Jun. 23, 2020, the entire content of which are incorporated herein by reference.

TECHNICAL FIELD

The present invention relates to a method for preparing isopropyl alcohol, and more particularly, to a method for separating isopropyl alcohol from a reaction product in an isopropyl alcohol preparation process with high purity, and effectively recovering unreacted products.

BACKGROUND

Isopropyl alcohol (IPA) has been used in a variety of applications, including applications such as a cleaning agent, in an electronic industry for manufacturing a semiconductor or a liquid crystal display (LCD).

An isopropyl alcohol preparation process uses, for example, propylene and water as raw materials. In this case, the propylene reacts with water to produce isopropyl alcohol.

The reaction product in the isopropyl alcohol preparation process contains isopropyl alcohol, unreacted propylene monomer, and unreacted water. In this case, isopropyl alcohol is separated and recovered, unreacted propylene monomer is recovered from the reaction product in the isopropyl alcohol preparation process, and the unreacted propylene monomer is reused in the isopropyl alcohol preparation process.

On the other hand, in the related art, an absorption tower was used to separate isopropyl alcohol and unreacted propylene monomer from the reaction product in the isopropyl alcohol preparation process. Specifically, the isopropyl alcohol preparation process is carried out by a vapor-phase reaction. In this case, the resulting vapor-phase reaction product was fed to a bottom of the absorption tower, isopropyl alcohol in the reaction product was dissolved by using water as a solvent and separated from the bottom of the absorption tower, and a stream containing a propylene monomer was separated from the top of the absorption tower. However, when such a method is used, a separation efficiency in the absorption tower is low, such that about 1% to 3% by weight of propylene monomer leaks from a bottom of the absorption tower. Therefore, to recover the leaked propylene monomer, two or more flash drums, two or more distillation columns, two or more compressors, and three or more condensers are additionally required, thereby complicating the process and increasing an investment cost and an equipment maintenance cost. In addition, because water is required in an amount of 25% by weight or more relative to a flow rate of the reaction product fed to the absorption tower, a lot of energy is used to recover water by separating water and isopropyl alcohol from a rear end of the absorption tower.

To solve the problems described above, a study was conducted to separate isopropyl alcohol and propylene monomer by condensing the entire amount of the vapor-phase reaction product in the isopropyl alcohol preparation process and feeding the condensed vapor-phase reaction product to a stripper in a liquid-phase. However, even in this case, a lot of energy is used to condense the vapor-phase reaction product; a lot of energy is used in a reboiler of the stripper; and a complicated subsequent process for recovering the leaked propylene monomer is still required because about 1% to 2% by weight of propylene monomer still leaks from a bottom of the stripper.

SUMMARY

An objective of the present invention is to provide a method for effectively separating isopropyl alcohol and a propylene monomer from the reaction product in the isopropyl alcohol preparation process in a simple process.

That is, the present invention may provide a method of preventing a propylene monomer from leaking from a bottom of a stripper and easily recovering the propylene monomer recovered from the top of the stripper to a reactor of a reaction unit, by generating a reaction product in the reaction unit, separating the reaction product into a vapor-phase first discharge stream and a liquid-phase second discharge stream, and then feeding each of the first discharge stream and the second discharge stream to the stripper.

In one exemplary aspect, there is provided a method for preparing isopropyl alcohol, the method including: feeding a feed stream containing a propylene monomer and water to a reaction unit to allow the propylene monomer and the water to react to each other, resulting in a reaction product containing isopropyl alcohol, the propylene monomer, and the water; feeding each of a first discharge stream containing a vapor-phase reaction product discharged from the reaction unit and a second discharge stream containing a liquid-phase reaction product discharged from the reaction unit to a stripper; and separating a top discharge stream containing the propylene monomer and a bottom discharge stream containing the water and the isopropyl alcohol, from the stripper, wherein the first discharge stream is condensed through a first heat exchanger and is fed to the stripper in a liquid-phase.

According to an exemplary embodiment of the method for preparing isopropyl alcohol, a reaction product in an isopropyl alcohol preparation process is separated into a vapor-phase first discharge stream and a liquid-phase second discharge stream, and each of the vapor-phase first discharge stream and the liquid-phase second discharge stream is fed to a stripper, thereby increasing separation efficiency in a stripper.

In addition, the bottom discharge stream of the stripper and the first discharge stream may be heat-exchanged, thereby saving energy for heating the bottom discharge stream of the stripper.

Further, no complicated subsequent process may be required to separate the propylene monomer from the bottom discharge stream of the stripper by preventing the propylene monomer from leaking from a bottom of the stripper, thereby reducing an investment cost and a facility maintenance cost.

In addition, a forward reaction of an equilibrium reaction in a reactor may be promoted by minimizing the content of isopropyl alcohol in a top discharge stream of the stripper that is circulated to the reactor, thereby increasing the production amount of isopropyl alcohol.

DETAILED DESCRIPTION

Figure 1:
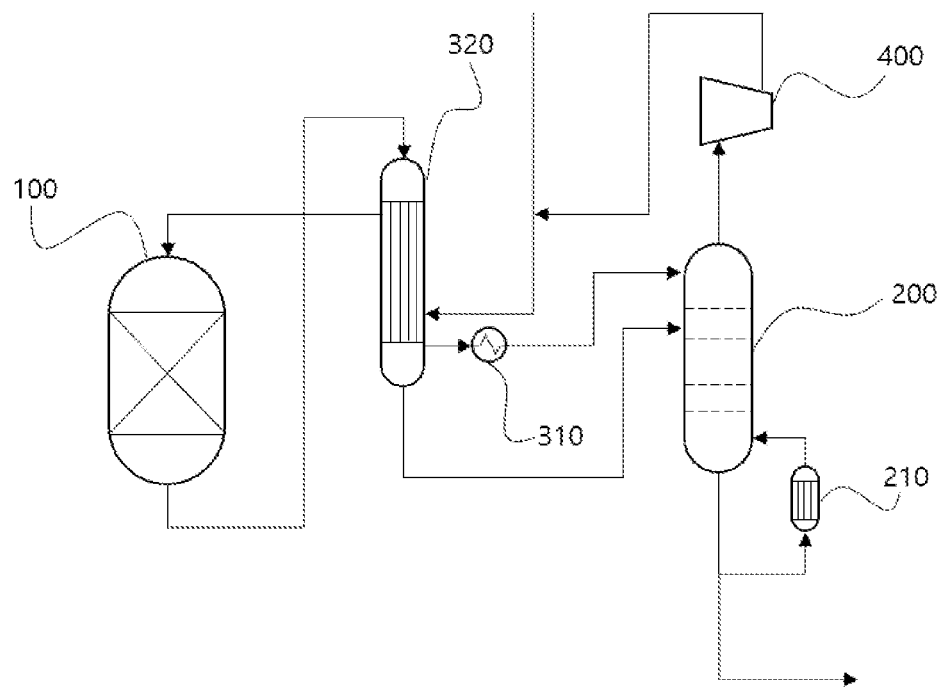
FIGS. 1 and 2 are a process flow diagram illustrating a method for preparing isopropyl alcohol according to an embodiment of the present invention.

The terms and words used in the detailed description and claims of the present invention should not be interpreted as being limited to conventional or dictionary meanings, but should be interpreted as having meanings and concepts meeting the technical ideas of the present invention based on a principle that the inventors can appropriately define the concepts of terms in order to describe their own inventions in the best mode.

The term "stream" used herein may refer to a flow of fluid in a process, and may also refer to fluid itself flowing in a pipe. Specifically, the "stream" may refer to both the fluid itself flowing in a pipe connecting respective apparatuses to each other and the flow of fluid. In addition, the fluid may refer to gas or liquid.

Hereinafter, in order to help understand the present invention, the present invention will be described in more detail with reference to FIGS. 1 and 2.

According to an exemplary embodiment of the present invention, there is provided a method for preparing isopropyl alcohol. The isopropyl alcohol may be produced by reacting a propylene monomer with water in a vapor phase. Specifically, a feed stream containing a propylene monomer and water may be fed to a reaction unit, and a reaction product produced in the reaction unit may include isopropyl alcohol, unreacted propylene monomer, and unreacted water. In this case, isopropyl alcohol is separated and recovered and unreacted propylene monomer is recovered, from the reaction product, and the unreacted propylene monomer is reused in the isopropyl alcohol preparation process.

On the other hand, in the related art, an absorption tower was used to separate isopropyl alcohol and unreacted propylene monomer from the reaction product. Specifically, the isopropyl alcohol preparation process is carried out by a vapor-phase reaction. In this case, the resulting vapor-phase reaction product was fed to a bottom part of the absorption tower, and isopropyl alcohol in the reaction product was dissolved by using a solvent and separated from the bottom of the absorption tower, and a stream containing a propylene monomer was separated from the top of the absorption tower. However, when such a method is used, a separation efficiency in the absorption tower is low, such that about 1% to 3% by weight of propylene monomer leaks from a bottom of the absorption tower. Therefore, to recover the leaked propylene monomer two or more flash drums, two or more distillation columns, two or more compressors, and three or more condensers are additionally required, thereby complicating the process and increasing an investment cost and an equipment maintenance cost. In addition, since a solvent is required in an amount of 25% by weight or more relative to flow rate of the reaction product fed to the absorption tower, a lot of energy is used to recover water by separating water and isopropyl alcohol from a rear end of the absorption tower.

To solve the above problems, a study was conducted to separate isopropyl alcohol and a propylene monomer by condensing the entire amount of a vapor-phase reaction product in the isopropyl alcohol preparation process and feeding the condensed vapor-phase reaction product to a stripper in a liquid-phase. However, even in this case, a lot of energy is used to condense the vapor-phase reaction product; a lot of energy is used in a reboiler of the stripper; and a complicated subsequent process for recovering the leaked propylene monomer is still required because about 1% to 2% by weight of propylene monomer still leaks from the bottom of the stripper.

Thus, to solve the above-mentioned conventional problems, the present invention provides a method of maximizing the separation efficiency of isopropyl alcohol and a propylene monomer to simplify a conventional complex process, and reducing energy consumption in the process.

According to an exemplary embodiment of the present invention, there is provided a method for preparing isopropyl alcohol, the method including: feeding a feed stream containing a propylene monomer and water to a reaction unit to allow the propylene monomer and the water to react to each other, resulting in a reaction product containing isopropyl alcohol, the propylene monomer, and the water; feeding each of a first discharge stream containing a vapor-phase reaction product discharged from the reaction unit and a second discharge stream containing a liquid-phase reaction product discharged from the reaction unit to a stripper 200; and separating a top discharge stream containing the propylene monomer and a bottom discharge stream containing the water and the isopropyl alcohol, from the stripper 200, wherein the first discharge stream is condensed through a first heat exchanger 310 and is fed to the stripper 200 in a liquid-phase.

According to an exemplary embodiment of the present invention, a molar ratio of water to the propylene monomer contained in the feed stream fed to the reaction unit may be 0.3 to 0.5, 0.35 to 0.5, or 0.35 to 0.45. The molar ratio of water to the propylene monomer in the feed stream fed to the reaction unit is satisfied with the above range, such that the forward reaction of the equilibrium reaction may be facilitated, and a reverse reaction may be prevented from proceeding, thereby increasing the production amount of isopropyl alcohol.

The reaction unit may include a reactor 100 and one or more heat exchangers. Specifically, the feed stream containing the propylene monomer and water may be fed to the reactor 100 of the reaction unit and subjected to a vapor-phase reaction in the reactor 100 to generate a reaction product.

The operating pressure in the reactor 100 may be, for example, 30 kg/cm$^2$·g to 50 kg/cm$^2$·g, 35 kg/cm$^2$·g to 50 kg/cm$^2$·g, or 35 kg/cm$^2$·g to 45 kg/cm$^2$·g. Isopropyl alcohol may be produced by the vapor-phase reaction using a propylene monomer and water by operating the reactor 100 at a pressure within the above range.

The vapor-phase reaction product may be discharged from the reactor 100 by the vapor-phase reaction of the propylene monomer with water in the reactor 100. In this case, the temperature of the vapor-phase reaction product discharged from the reactor 100 may be, for example, 200° C. to 220° C., 205° C. to 220° C., or 205° C. to 215° C.

According to an exemplary embodiment of the present invention, the vapor-phase reaction product discharged from the reactor 100 may be partially condensed into a liquid-phase reaction product while passing through one or more heat exchangers, and the remainder may exist in the vapor-phase reaction product. As an example, the vapor-phase reaction product discharged from the reactor 100 may be separated into a first discharge stream containing the vapor-phase reaction product and a second discharge stream containing the liquid-phase reaction product while passing through the second heat exchanger 320. In this case, the first discharge stream and the second discharge stream may be separated and discharged through separate pipes formed in the second heat exchanger 320, or may be separated through a gas-liquid separation device installed at a rear end of the second heat exchanger 320.

According to an embodiment of the present invention, the vapor-phase reaction product discharged from the reactor 100 may exchange heat with the feed stream fed to the reactor 100 from one or more heat exchangers. Specifically, the vapor-phase reaction product discharged from the reactor 100 is partially condensed while passing through at least one heat exchanger, and the feed stream may be heated while passing through one or more heat exchangers before being fed to the reactor 100. In this case, a temperature of the feed stream before passing through the one or more heat exchangers may be, for example, 90° C. to 130° C., 100° C. to 120° C., or 105° C. to 115° C. In addition, the temperature of the feed stream after passing through the one or more heat exchangers may be, for example, 170° C. to 210° C., 180° C. to 200° C., or 185° C. to 195° C. Further, the temperature of the first discharge stream and the second discharge stream passing through the one or more heat exchangers may be, for example, 105° C. to 150° C., 110° C. to 140° C., or 110° C. to 130° C.

The vapor-phase discharge stream of the reactor 100 may be separated into the first discharge stream containing the vapor-phase reaction product and the second discharge stream containing the liquid-phase reaction product by heat-exchanging the discharge stream of the reactor 100 with the feed stream, and at the same time, the feed stream may be preheated and fed to the reactor 100. Thus, energy for heating may be reduced by feeding the feed stream to the reactor 100, and the separation efficiency in a subsequent separation process using the stripper may be increased by controlling the composition of the first discharge stream and the second discharge stream.

According to an exemplary embodiment of the present invention, the first discharge stream may contain 85% to 95% by weight of propylene monomer, 4% to 8% by weight of isopropyl alcohol, and 1% to 5% by weight of water. Specifically, it can be seen that the first discharge stream has a very high content of propylene monomer and a very low content of isopropyl alcohol and water.

In addition, the second discharge stream may contain 1% to 10% by weight of propylene monomer, 5% to 15% by weight of isopropyl alcohol, and 80% to 90% by weight of water. Specifically, it can be seen that the second discharge stream has a very low content of propylene monomer and a very high content of water. In this case, the content of isopropyl alcohol contained in the second discharge stream may be higher than that contained in the first discharge stream.

According to an exemplary embodiment of the present invention, a flow rate ratio of the first discharge stream to the second discharge stream discharged from the reaction unit may be 5 to 11, 6 to 10, or 7 to 9. As described herein, in the process of heat-exchanging the discharge stream of the reactor 100 with the feed stream in one or more heat exchangers, the flow rate ratio of the first discharge stream to the second discharge stream may be controlled to 5 to 11 by cooling the discharge stream of the reactor 100 to a temperature of 105° C. to 150° C.

According to an exemplary embodiment of the present invention, the first discharge stream and the second discharge stream from the second heat exchanger 320 may be separated by being fed to the stripper 200 as respective streams. Specifically, in the stripper 200, the top discharge stream containing a propylene monomer and the bottom discharge stream containing water and isopropyl alcohol may be separated.

The first discharge stream containing the vapor-phase reaction product may be condensed through the first heat exchanger 310 and fed to the stripper 200 in a liquid state. For example, in the first heat exchanger 310, the first discharge stream from the second heat exchanger 320 may be condensed by using a separate refrigerant or by performing heat-exchange with the stream in the process. In this case, if necessary, to condense the first discharged stream and feed the condensed first discharge stream to the stripper 200 in a liquid state, a cooler (not illustrated) may be additionally used in addition to the first heat exchanger 310. In this case, the first discharge stream is primarily condensed through the first heat exchanger 310, the primarily condensed stream is secondarily cooled in a cooler (not illustrated), the refrigerant used in the cooler (not illustrated) may be replaced with inexpensive cooling water, and the amount of the cooling water used may be minimized.

Since the first discharge stream and the second discharge stream have different components, the separation efficiency of isopropyl alcohol and a propylene monomer may be improved by appropriately controlling feed stages of the first discharge stream and the second discharge stream fed to the stripper 200.

According to an exemplary embodiment of the present invention, the first discharge stream may be fed to an upper part of the stripper 200. For example, the first discharge stream may be condensed through the first heat exchanger 310, and the condensed first discharge stream may be fed to 1st stage of the stripper 200.

In comparison, the second discharge stream may be fed to the side of the stripper 200 at a lower height than the first discharge stream. For example, the second discharge stream may be fed to either 10% to 35% of stages, or 15% to 27% of stages of the number of theoretical stages of the stripper 200. For example, when the number of theoretical stages of the stripper 200 is 100 stages, the uppermost stage may be a 1st stage and the lowermost stage may be a 100th stage, and 3% to 10% of the stages in the number of theoretical stages of the stripper 200 may mean 3rd to 10th stage of the stripper 200. The second discharge stream has a low content of propylene and a high content of isopropyl alcohol and water compared to the first discharge stream. Thus, an operating cost of the reboiler 210 installed under the stripper 200 may be reduced by feeding the second discharge stream to the stage in the range of the stripper 200, and the separation efficiency of isopropyl alcohol and water may be improved by securing a rectifying unit in the stripper 200.

According to an exemplary embodiment of the present invention, the operating pressure of the stripper 200 may be normal pressure. The propylene monomer may be separated from the top discharge stream with high purity and circulated to the reactor 100 of the reaction unit without further purification by operating the stripper 200 at normal pressure. More specifically, by minimizing the content of isopropyl alcohol in the top discharge stream of the stripper 200, when isopropyl alcohol is circulated to the reactor 100, the reverse reaction of the equilibrium reaction may be facilitated, thereby solving the problem of decreasing the production amount of isopropyl alcohol. In addition, it is possible to eliminate the complicated subsequent process for recovering propylene from the bottom discharge stream by preventing the propylene monomer from being present in the bottom discharge stream of the stripper 200.

According to an exemplary embodiment of the present invention, the top discharge stream of the stripper 200 may be heat-exchanged with the discharge stream of the reactor 100 while passing through one or more heat exchangers of the reaction unit, and then fed to the reactor 100. In this case, the temperature of the top discharge stream of the stripper 200 may be, for example, −10° C. to 5° C., −5° C. to 5° C., or −5° C. to 0° C. The top discharge stream of the stripper 200 may be mixed with the feed stream to pass through one or more heat exchangers of the reaction unit.

According to an exemplary embodiment of the present invention, the bottom discharge stream of the stripper 200 may be a stream containing isopropyl alcohol and water without the propylene monomer. In this case, the temperature of the bottom discharge stream of the stripper 200 may be, for example, 40° C. to 70° C., 40° C. to 60° C., or 50° C. to 60° C. As described above, some streams of the low-temperature bottom discharge stream of the stripper 200 may be fed to the reboiler 210, heated in the reboiler 210, and then refluxed to the stripper 200. In addition, the remaining streams of the bottom discharge stream of the stripper 200 that is not fed to the reboiler 210 may be fed to a purification unit of isopropyl alcohol. According to an exemplary embodiment of the present invention, the low-temperature bottom discharge stream of the stripper 200 may be fed to the first heat exchanger 310 and the remaining streams may be fed to the purification unit of isopropyl alcohol. Some streams of the bottom discharge stream of the stripper 200, subject to heat-exchange with the first discharge stream in the first heat exchanger 310 may, be heated using the heat of condensation of the first discharge stream, and some streams of the bottom discharge stream of the heated stripper 200 may be refluxed to the stripper 200.

The remaining streams of the bottom discharge stream of the stripper 200 that is not fed to the first heat exchanger 310 may be fed to an isopropyl alcohol purification unit to separate high purity isopropyl alcohol from which water has been removed. In this case, the water separated from the isopropyl alcohol purification unit may be fed to the reactor 100 and be reused, and in this case impurities such as propylene monomer or isopropyl alcohol are not included, making it easier to control the molar ratio of water to propylene monomer in preparing isopropyl alcohol in the reactor 100.

According to an exemplary embodiment of the present invention, devices such as a distillation column (not illustrated), a condenser (not illustrated), a reboiler (not illustrated), a valve (not illustrated), a pump (not illustrated), a separator (not illustrated), and a mixer (not illustrated) may be additionally installed and used, if necessary, in the method for preparing isopropyl alcohol.

The method for preparing isopropyl alcohol according to exemplary embodiments of the present invention has been described and has been shown in the drawings herein, but only essential configurations for understanding the present invention have been described and have been illustrated in the drawings, and processes and apparatuses that are not separately described and illustrated, in addition to processes and apparatus described above and illustrated in the drawings, may be appropriately applied and used to carry out the method for preparing isopropyl alcohol according to the present invention.

Hereinafter, the present invention will be described in detail with reference to the following examples. However, the following examples are intended to be purely exemplary of the invention. It is apparent to those skilled in the art that various changes and modifications can be made within the scope and spirit of the present invention and that the present invention is not limited thereto.

EXAMPLES

Example 1

As shown in the process flow diagram illustrated in FIG. 1, isopropyl alcohol (IPA) was prepared, and the unreacted product and isopropyl alcohol were separated.

Specifically, a feed stream was fed at a flow rate of 134 ton/hr to the reactor 100 operated at a pressure of 40 kg/cm$^2$·g, and the ratio of water ($H_2O$) to propylene monomer (PP) in the feed stream was controlled to 0.4. In this case, the feed stream passed through the second heat exchanger 320 and then was fed to the reactor 100.

The discharge stream of the reactor 100 was separated into a first discharge stream and a second discharge stream while passing through the second heat exchanger 320 and then discharged, and the first discharge stream was condensed in the first heat exchanger 310 and then fed to 1st stage of the stripper 200. In addition, the second discharge stream was fed to 5th stage of the stripper 200.

The stripper 200 was operated at normal pressure, the top discharge stream of the stripper 200 was compressed using a compressor 400 and then mixed with the feed stream and circulated to the reactor 100. Some streams of the bottom discharge stream of the stripper 200 were fed to the reboiler 210 and then refluxed, and the remaining streams were fed to the isopropyl alcohol purification unit. In this case, the total number of stages of the stripper 200 was 19 stages.

As a result, flow rates, temperatures, components, and feed stages of the stripper 200 of the first and second discharge streams are shown in Table 1 below. In addition, the flow rates, temperatures, components of the top and bottom discharge streams of the stripper 200, and the amount of stream used to heat the bottom discharge stream of the stripper 200 are shown in Table 2 below.

Example 2

Figure 2:
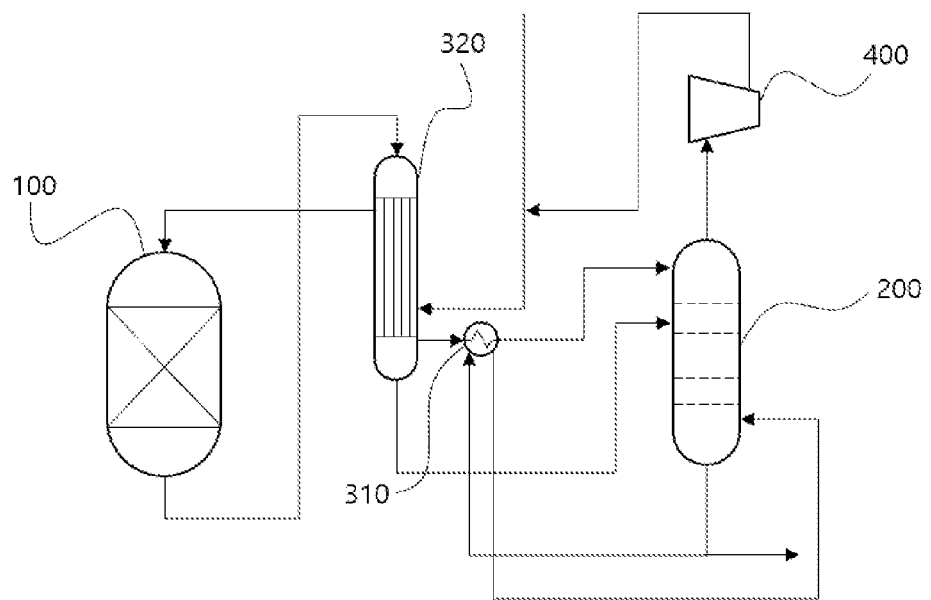

As shown in the process flow diagram illustrated in FIG. 2, the isopropyl alcohol was prepared, and the unreacted product and isopropyl alcohol were separated.

Specifically, the feed stream was fed at a flow rate of 134 ton/hr to the reactor 100 operated at a pressure of 40 kg/cm$^2$·g, and the ratio of water to propylene monomer in the feed stream was controlled to 0.4. In this case, the feed stream passed through the second heat exchanger 320 and then was fed to the reactor 100.

The discharge stream of the reactor 100 was separated into a first discharge stream and a second discharge stream while passing through the second heat exchanger 320 and then discharged, and the first discharge stream was condensed in the first heat exchanger 310 and then fed to the 1st stage of the stripper 200. In addition, the second discharge stream was fed to the 5th stage of the stripper 200. In this case, if necessary, a separate condenser (not illustrated) was placed to further condense the uncondensed first discharge stream using cooling water.

The stripper 200 was operated at normal pressure, the top discharge stream of the stripper 200 was compressed to the pressure of the reactor 100 using a compressor 400, mixed with the feed stream, and then circulated to the reactor 100. Some streams of the bottom discharge stream of the stripper 200 were fed to the first heat exchanger 310 and then refluxed, and the remaining streams were fed to the isopropyl alcohol purification unit. In this case, the total number of stages of the stripper 200 was 19 stages.

As a result, the flow rates, temperatures, components, and feed stages of the stripper 200 of the first and second discharge streams are shown in Table 1 below. In addition, the flow rates, temperatures, components of the top and bottom discharge streams of the stripper 200, and the amount of stream used to heat the bottom discharge stream of the stripper 200 are shown in Table 2 below.

Example 3

Isopropyl alcohol was prepared in the same manner as described in Example 2, except that the temperatures of the first discharge stream and the second discharge stream were controlled to 110° C.

As a result, the flow rates, temperatures, components, and feed stages of the stripper 200 of the first and second discharge streams are shown in Table 1 below. In addition, the flow rates, temperatures, components of the top and bottom discharge streams of the stripper 200, and the amount of stream used to heat the bottom discharge stream of the stripper 200 are shown in Table 2 below.

Example 4

Isopropyl alcohol was prepared in the same manner as described in Example 2, except that the second discharge stream was fed to the 3rd stage of the stripper 200.

As a result, the flow rates, temperatures, components, and feed stages of the stripper 200 of the first and second discharge streams are shown in Table 1 below. In addition, the flow rates, temperatures, components of the top and bottom discharge streams of the stripper 200, and the amount of stream used to heat the bottom discharge stream of the stripper 200 are shown in Table 2 below.

COMPARATIVE EXAMPLES

Comparative Example 1

Figure 3:
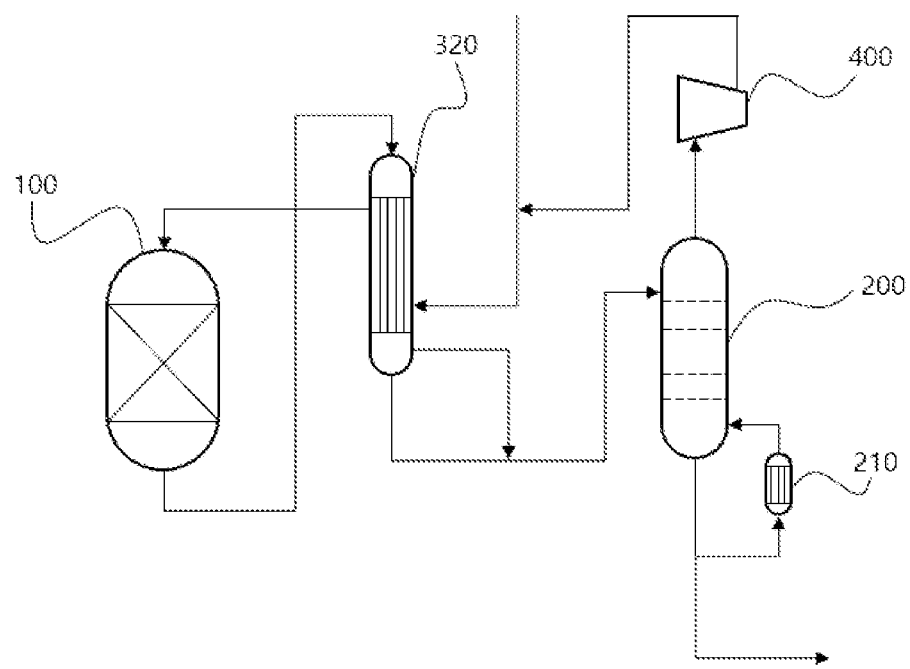
FIG. 3 is a process flow diagram illustrating a method for preparing isopropyl alcohol according to comparative examples.

As shown in the process flow diagram illustrated in FIG. 3, isopropyl alcohol was prepared, and the unreacted product and isopropyl alcohol were separated.

Specifically, the feed stream was fed at a flow rate of 134 ton/hr to the reactor 100 operated at a pressure of 40 kg/cm²·g, and the ratio of water to propylene monomer in the feed stream was controlled to 0.4. In this case, the feed stream passed through the second heat exchanger 320 and then was fed to the reactor 100.

The discharge stream of the reactor 100 was mixed with the first discharge stream and the second discharge stream separated while passing through the second heat exchanger 320 and fed to the 1st stage of the stripper 200.

The stripper 200 was operated at normal pressure, the top discharge stream of the stripper 200 was compressed to the pressure of the reactor 100 using a compressor 400, mixed with the feed stream, and then circulated to the reactor 100. Some streams of the bottom discharge stream of the stripper 200 were fed to the reboiler 210 and then refluxed, and the remaining streams were fed to the isopropyl alcohol purification unit. In this case, the total number of stages of the stripper 200 was 19 stages.

As a result, the flow rates, temperatures, components, and feed stages of the stripper 200 of the first and second discharge streams are shown in Table 1 below. In addition, the flow rates, temperatures, components of the top and bottom discharge streams of the stripper 200, and the amount of stream used to heat the bottom discharge stream of the stripper 200 are shown in Table 2 below.

TABLE 1

|  |  | Example 1 | Example 2 | Example 3 | Example 4 | Comp. Example 1 |
|---|---|---|---|---|---|---|
| Flow rate of first discharge stream (ton/hr) |  | 120 | 120 | 118 | 120 | 120 |
| Flow rate of second discharge stream (ton/hr) |  | 14 | 14 | 16 | 14 | 14 |
| Temperature of first discharge stream (° C.) |  | 124 | 124 | 110 | 124 | 124 |
| Temperature of second discharge stream (° C.) |  | 124 | 124 | 110 | 124 | 124 |
| Feed stage of first discharge stream |  | 1st stage | 1st stage | 1st stage | 1st stage | 1st stage |
| Feed stage of second discharge stream |  | 5th stage | 5th stage | 5th stage | 3rd stage | 5th stage |
| First discharge stream | PP (wt %) | 91.0 | 91.0 | 92.5 | 91.0 | 91.0 |
|  | IPA (wt %) | 6.2 | 6.2 | 5.8 | 6.2 | 6.2 |
|  | H$_2$O (wt %) | 2.8 | 2.8 | 1.7 | 2.8 | 2.8 |
| Second discharge stream | PP (wt %) | 5.8 | 5.8 | 5.0 | 5.8 | 5.8 |
|  | IPA (wt %) | 6.8 | 6.8 | 9.7 | 6.8 | 6.8 |
|  | H$_2$O (wt %) | 87.4 | 87.4 | 87.4 | 87.4 | 87.4 |

TABLE 2

|  |  | Example 1 | Example 2 | Example 3 | Example 4 | Comp. Example 1 |
|---|---|---|---|---|---|---|
| Flow rate of top discharge stream (ton/hr) | | 109 | 109 | 108 | 109 | 126 |
| Flow rate of bottom discharge stream (ton/hr) | | 25 | 25 | 26 | 25 | 8 |
| Temperature of top discharge stream (° C.) | | −5 | −5 | −8 | −5 | 55 |
| Temperature of bottom discharge stream (° C.) | | 58 | 58 | 52 | 58 | 95 |
| Top discharge stream | PP (wt %) | 99.6 | 99.6 | 99.7 | 99.6 | 86.4 |
| | IPA (wt %) | 0.3 | 0.3 | 0.2 | 0.3 | 6.4 |
| | $H_2O$ (wt %) | 0.1 | 0.1 | 0.1 | 0.1 | 7.2 |
| Bottom discharge stream | PP (wt %) | 0 | 0 | 0 | 0 | 0 |
| | IPA (wt %) | 32.2 | 32.2 | 32.3 | 32.2 | 4.9 |
| | $H_2O$ (wt %) | 67.8 | 67.8 | 67.7 | 67.8 | 95.1 |
| Amount of stream used (Gcal/hr) | | 2.1 | 0 | 0 | 0 | 0.5 |

It was confirmed from Tables 1 and 2 that in Example 1, in which the first discharge stream and the second discharge stream discharged from the reaction unit by the method according to the present invention are fed to the stripper 200 as independent streams, the content of the isopropyl alcohol and water was very small in the top discharge stream of the stripper 200, and no propylene monomer was present in the bottom discharge stream of the stripper 200.

In addition, it could be confirmed from Example 2 that there was no need to use stream for heating the bottom discharge stream of the stripper 200.

In addition, it could be confirmed from Example 3 that separation effectively occurred in the stripper 200.

Further, it could be confirmed from Examples 1, 2, and 4, in which the second discharge stream was fed to 15% to 27% of the number of stages of the stripper 200, that separation effectively occurred in the stripper 200.

In comparison, in Comparative Example 1, the isopropyl alcohol was prepared in the same manner as described in Example 1, except that when the first and second discharge streams were mixed and fed to the 1st stage of the stripper 200, the first discharge stream was not condensed and was injected into the stripper in a gaseous state. Thus, there is a problem in that the isopropyl alcohol and water contained in the first discharge stream were discharged from the top of the stripper 200 in a gaseous state. In addition, as the second discharge stream is fed to the 1st stage of the stripper 200, the isopropyl alcohol and water contained in the second discharge stream did not pass through the rectifying unit. Therefore, there is a problem in that most of the isopropyl alcohol and water are discharged from the top of the stripper 200. That is, in the case of Comparative Example 1, there is a problem in that isopropyl alcohol and water are not discharged to the bottom of the stripper 200. In addition, in the case of Comparative Example 1, the temperature increased as the content of the isopropyl alcohol decreased and the content of the water increased in the bottom discharge stream of the stripper 200. Therefore, it was not possible to implement a sufficient temperature for cooling the first discharge stream through the heat exchange.

The invention claimed is:

1. A method for preparing isopropyl alcohol, the method comprising:
    feeding a feed stream containing a propylene monomer and water to a reactor, wherein the propylene monomer and the water react to form a reaction product comprising isopropyl alcohol, the propylene monomer, and the water;
    separating a discharge stream of the reactor into a first discharge stream containing a vapor-phase reaction product and a second discharge stream containing a liquid-phase reaction product while passing through a second heat exchanger;
    feeding each of the first discharge stream and the second discharge stream to a stripper, wherein the vapor-phase reaction product is condensed through a first heat exchanger and fed to the stripper in a liquid-phase; and
    separating a top discharge stream and a bottom discharge stream from the stripper, wherein the top discharge stream comprises the propylene monomer and the bottom discharge stream comprises the water and the isopropyl alcohol.

2. The method for preparing isopropyl alcohol of claim 1, wherein a temperature of each of the first discharge stream and the second discharge stream is 105° C. to 150° C.

3. The method for preparing isopropyl alcohol of claim 2, wherein a temperature of each of the first discharge stream and the second discharge stream is 110° C. to 130° C.

4. The method for preparing isopropyl alcohol of claim 1, wherein a flow rate ratio of the first discharge stream to the second discharge stream is 5 to 11.

5. The method for preparing isopropyl alcohol of claim 1, wherein the first discharge stream comprises the propylene monomer in an amount of 85% to 95% by weight, and
    wherein the second discharge stream comprises the propylene monomer in an amount of 1% to 10% by weight.

6. The method for preparing isopropyl alcohol of claim 1, wherein an amount of the isopropyl alcohol in the second discharge stream is higher than an amount of the isopropyl alcohol in the first discharge stream.

7. The method for preparing isopropyl alcohol of claim 1, wherein the first discharge stream is fed to a top side of the stripper, and
    wherein the second discharge stream is fed to a side of the stripper at a lower height than the first discharge stream.

8. The method for preparing isopropyl alcohol of claim 7, wherein the first discharge stream is fed to the first stage of the stripper, and wherein the second discharge stream is fed to a stage, which is 10% to 35% of the number of theoretical stages of the stripper.

9. The method for preparing isopropyl alcohol of claim 8, wherein the second discharge stream is fed to a stage, which is 15% to 27% of the number of theoretical stages of the stripper.

10. The method for preparing isopropyl alcohol of claim 1, wherein the discharge stream of the reactor is heat-exchanged with the feed stream fed to the reactor in the second heat exchanger.

11. The method for preparing isopropyl alcohol of claim 1, wherein the top discharge stream of the stripper is heat-exchanged with the discharge stream of the reactor while passing through the second heat exchanger, and is then fed to the reactor.

12. The method for preparing isopropyl alcohol of claim 1, wherein the first discharge stream is heat-exchanged with the bottom discharge stream of the stripper in the first heat exchanger.

\* \* \* \* \*